(12) United States Patent
Hutcheson et al.

(10) Patent No.: US 6,243,219 B1
(45) Date of Patent: Jun. 5, 2001

(54) LASER LIGHT OPTICAL LIMITER

(75) Inventors: Ralph L. Hutcheson; Randy W. Equall, both of Bozeman, MT (US)

(73) Assignee: Scientific Materials Corporation, Bozeman, MT (US)

(*) Notice: Subject to any disclaimer, the term of this patent is extended or adjusted under 35 U.S.C. 154(b) by 0 days.

(21) Appl. No.: 09/342,716

(22) Filed: Jun. 29, 1999

Related U.S. Application Data

(63) Continuation-in-part of application No. 08/899,546, filed on Jul. 24, 1997, now abandoned.

(51) Int. Cl.[7] ............................. G02B 5/22; G02B 5/25; G02F 1/03
(52) U.S. Cl. ..................... 359/885; 359/244; 501/126
(58) Field of Search .............................. 359/244, 885; 501/110, 112, 126, 127; 372/11

(56) References Cited

PUBLICATIONS

Wood et al, SPIE, vol. 1692, pp. 2–14., 1992.*
Wolf et al, Proc. of OSA, p. 238–242 But Only Abst. Provided Herewith, NTIS, AN AD–A215 513/3/XAB, May 3, 1989.*
Crane et al, Materials for Optical Limiting, Symp., pp. 390; Abst. Only Herewith, Nov. 4, 1994.*
Morrison et al, NTIS An SD–A200/08/9/AB; Abst–Only Herewith, Oct. 1988.*

* cited by examiner

Primary Examiner—Nelson Moskowitz
(74) Attorney, Agent, or Firm—Laurence R. Letson

(57) ABSTRACT

Inorganic crystals having one or more species of dopant ions which are photo-reactive are used as visible and or infrared light optical limiters to protect against laser radiation exposure while permitting passage of the visible and or infrared light spectrum at least until exposed to high energy laser radiation. The dopant ions are selected from ions of transition metals. The exposure of these ions within the transparent crystalline matrix either photo-ionize or are elevated to an excited state and thereby absorb or otherwise attenuate the passage of the laser beam radiation sufficiently to protect human eyes or photo-sensitive equipment. The crystals may be fabricated into such items as lenses for use in eyeglasses or on shields of flight helmets to protect the eyes of aircraft pilots.

19 Claims, 6 Drawing Sheets

LASER LIGHT OPTICAL LIMITER

This Appln. is a C-I-P of Ser. No. 08/899,546 filed Jul. 24, 1997, Abnd.

STATEMENT OF GOVERNMENT INTEREST

This invention was made with partial support from the United States Government under Contract F33615-96-C-3416 awarded by the United States Air Force. The United States Government may have certain rights in this invention.

FIELD OF THE INVENTION

This invention relates to the protection of receptors sensitive to light in the visible and infrared (IR) regions of the electromagnetic spectrum, including but not limited to human eyes and optical detectors, and more specifically, to optical limiters, which allow passage of normal ambient light levels such as sunlight but prevent passage of high levels of light such as laser light, and which are comprised of substantially transparent material having a dopant that is photo-reactive.

BACKGROUND OF THE INVENTION

Visible and IR light receptors are capable of detecting electromagnetic radiation (light) at various intensity levels and at various wavelengths (colors) in the spectral region from approximately 400 nm to 5000 nm. Examples of such light receptors include but are not limited to the human eye and optical detectors/sensors which produce a response (thermal, electrical etc.) whenever illuminated.

The human eye, optical detectors/sensors and photo-receptors can be damaged by exposure to high intensities of light. For example, optical detectors can be exposed beyond their capabilities and destroyed by either continuous or short duration exposure to a laser beam. Similarly, the retina of the eye can be damaged by being exposed to a laser beam for only a brief period of time. In effect, the retina and the nerves within the retina are burned by the intense light of the laser beam.

In laboratory and industrial settings, protective glasses or goggles are commonly worn to protect the eyes from exposure to laser light. These eye protection devices are based on filtering techniques and, typically, are made from tinted or colored materials which may be selected for protection over specific wavelength ranges of laser light. Because of the coloration of these materials, light at wavelengths other than that of the laser light are attenuated. This restricts abroader portion of the spectrum, significantly altering the spectral features of the transmitted light. As a result, these protective glasses or shields typically have a disadvantage that the visual perception of the colors of objects and images observed are either altered or obscured. For example, goggles suitable for protection against green laser light at 532 nm, a frequency doubled Nd:YAG emission, or at 514.5 nm, an argon ion laser emission, are typically orange colored. This does not allow the wearer to perceive colors in the blue or green region of the visible spectrum.

While not all environments of usage require unaltered spectral transmission, there are numerous environments which have strict requirements for substantially unaltered spectral transmission. One specific example of such an environment is within an airplane cockpit. Many aircraft, both military and civilian, are using color coded instrumentation to display information for the pilot. Additionally, light displays projected on the wind screen or canopy and known as "heads-up" displays are color images which, if optically blocked, filtered or altered, may not be filly visible to the pilot.

The usage of lasers capable of blinding the cockpit crew of an aircraft has become a hazard for both military and commercial air traffic. It is therefore necessary to protect pilots' eyes from exposure to intense laser radiation. It is not feasible to block the transmission of all wavelengths of light commonly emitted by lasers using existing filtering techniques inasmuch as the ability of the pilot to observe both instrumentation inside the cockpit and other objects outside the cockpit would be so altered as to render the flight crew partially blinded or severely limited.

Photo-reactive optical limiters such as sun glasses that change color with higher visible light spectrum intensity are commercially available. The reaction time of the photo-reactive elements is quite slow, on the order of 1–90 seconds, and is definitely not fast enough to provide any protection from laser beams which may be of a pulsed or continuous wave type. Thus, a laser beam impinging on the eye through an eyeglass lens of this type will not be attenuated sufficiently or quickly enough to prevent damage to the eye.

A protective device capable of protecting the human eye or optical detectors from laser radiation must have a very fast photo-reactive response and yet must be of sufficient transparency in the spectral region applicable to a given light receptor to allow it to function. In the case of visual perception, the protective device to be effective must also permit, without distortion, observation of color images as advantageously used in certain environments requiring protection from exposure to laser radiation.

OBJECTS OF THE INVENTION

It is an object of the invention to protect photo-receptors, including but not limited to a human's eyes, and optical detectors from damage by exposure to high intensity lasers by changing the transmission characteristics of a transparent inorganic material interposed between the photo-receptor and the laser.

It is another object of the invention to alter the transmissibility of a transparent inorganic material by doping the inorganic material with photo-reactive ions to absorb or block the visible light in response to illumination of the doped material with high intensity laser radiation.

It is a further object of the invention to protect photo-receptors from the effects of laser light by altering the transmissibility of a transparent inorganic material having a photo-reactive dopant in response to laser light causing excited state absorption, photo-ionization, color center formulation, charge transfer and/or combinations of these processes.

SUMMARY OF THE INVENTION

Many inorganic materials are transition to visible and IR light. This transparency can be altered by the addition of dopant ions, either singly or in combinations. By adding dopants selected from the group of transition metal ions (elements with atomic numbers between 22 and 30), with the dopant levels in the range from one (1) percent to twenty (20) percent by weight for each dopant, the material containing these ions can become opaque to specific wavelengths of light whenever exposed to high intensity laser radiation. The transmission characteristics of such doped materials are initially determined by the host lattice and the ground state (lowest energy state) absorption bands of the dopant ions. Exposure of the material to laser light can induce new absorption bands in the material, referred to as photo-induced absorption (PIA). If the new absorption bands occur at the same wavelength as the laser light, the transmission of the laser light is substantially reduced or limited.

There are numerous processes in doped inorganic materials that have the capability of limiting the transmission of intense laser radiation including excited state absorption (ESA), photo-ionization, color center formation, charge transfer and trapping, and combinations of these processes. For example, at an intensity sufficient to cause damage to eyes or photo-detectors/sensors, light incident on the material is absorbed by the dopant ions that are originally in the ground state, thereby exciting the ions to an intermediate higher energy state. Ions in this intermediate energy state have substantially stronger absorption characteristics than the ions in the ground state and can further absorb light exciting the ions to even higher energy states. This process is referred to as excited state absorption. The reduction in transmission due to this process is significant when a sufficient number of ions have been excited to the intermediate level. As a result, low intensities of light pass through the material substantially unaltered while the transmission of high intensity laser light is significantly reduced. The opaque region is confined to the volume of the material which has been exposed to the high intensity laser radiation.

The transmission of high intensity laser light can also be limited by charge transfer and trapping processes. In these types of processes, dopant ions in the material interact with the laser light which excites the ions to a higher energy state. Excitation of the ions to this higher energy state may occur through direct absorption of a photon of sufficient energy, or through a variety of other mechanisms including ESA or two photon absorption. Ions in this higher energy state interact with the host lattice or other dopant ions resulting in the release of an electron by the excited dopant ions. If an ion was originally in an $N^+$ valance state, this process increases the valance state of the ions to $(N+1)^+$ and is typically referred to as photo-ionization. The electron released by the excited dopant ion can recombine with the ion, become trapped in the lattice creating a color center, or combine with some other dopant ion in the material changing its valance state (for example from $M^+$ to $(M-1)^+$). Recombination of the electron with the photo-ionized dopant ion results in recovery of the material to its original transmission state. Formation of color centers or the transfer of the electron to another dopant ion changes the absorption characteristics of the material and can result in optical limiting. In this case, the transmission of light through the material is determined by the absorption characteristics of the dopant ion in the $(N+1)^+$ valance state, the color centers and/or the new valance state of ions that have captured the electron. If the absorption bands induced by the laser light occur in the same wavelength region as the laser, these processes will reduce/limit the transmission of the laser light.

These excited state absorption, photo-ionization and charge transfer processes are reversible, allowing for recovery of the material transmission characteristics to the original state. For the case of ESA, the material spontaneously recovers through decay of the electron from the final excited state to the ground state. This occurs by spontaneous emission or by energy transfer to the host lattice (generation of phonons which result in the generation of heat). For the case of photoionization and subsequent charge transfer, the material can spontaneously recover upon recombination of the electron with the photo-ionized dopant ion or optical transmission can be restored by supplying energy to the material. For example, it may be possible to heat the material providing thermal energy to the electron to free it from the trap in the lattice, allowing it to reduce the photo-ionized dopant ions to their original valance state. This reversal process may also be accomplished by absorption of light (photons) by the trapped electron, freeing the electron from the trap and allowing recombination with the photoionized dopant ion.

The materials used to demonstrate this invention were single crystals doped with transition metal ions grown using conventional Czochralski crystal growth methods.

Crystals of yttrium orthoaluminate ($YAlO_3$), yttrium aluminum garnet ($Y_3Al_5O_{12}$, commonly referred to as YAG), and gadolinium gallium garnet ($Gd_3Ga_5O_{12}$, commonly referred to as GGG) doped with manganese (Mn), combinations of Mn and cobalt (Co), or combinations of Mn and calcium (Ca) were shown to exhibit ESA and charge transfer and trapping which resulted in the limiting of the transmission of laser light at selected wavelengths.

These doped crystalline materials were substantially transparent in the visible and IR regions of the spectrum. In the visible spectral region these crystals had slight or light color casts which depended on the specific combination of host and dopant ions as well as the valance state of the dopant ions.

The response time within which the optical limiting process occurred is less than 0.5 ns and the degree of optical limiting was intensity dependent, a very advantageous characteristic for eye protection.

A more complete understanding of the invention may be had from the accompanying drawings and the detailed description to follow.

A DETAILED DESCRIPTION OF THE INVENTION

Figure 1:
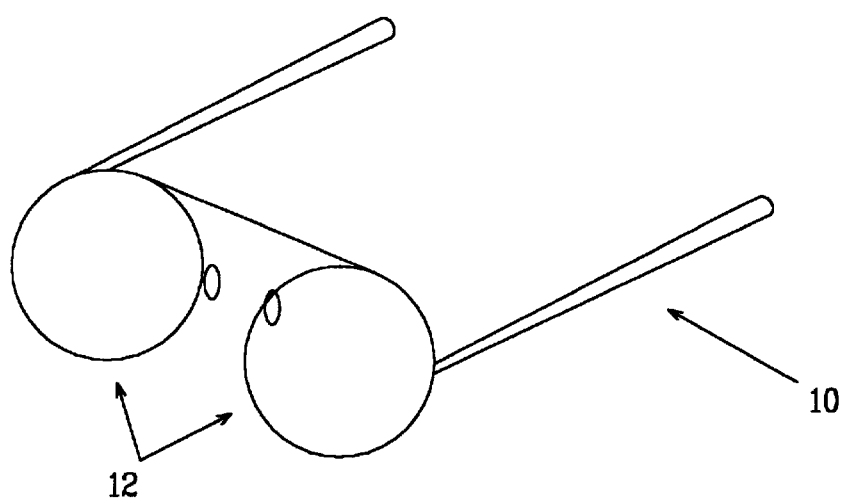
FIG. 1 is an illustration of a first embodiment of eye protection gear using the invention.
Figure 2:
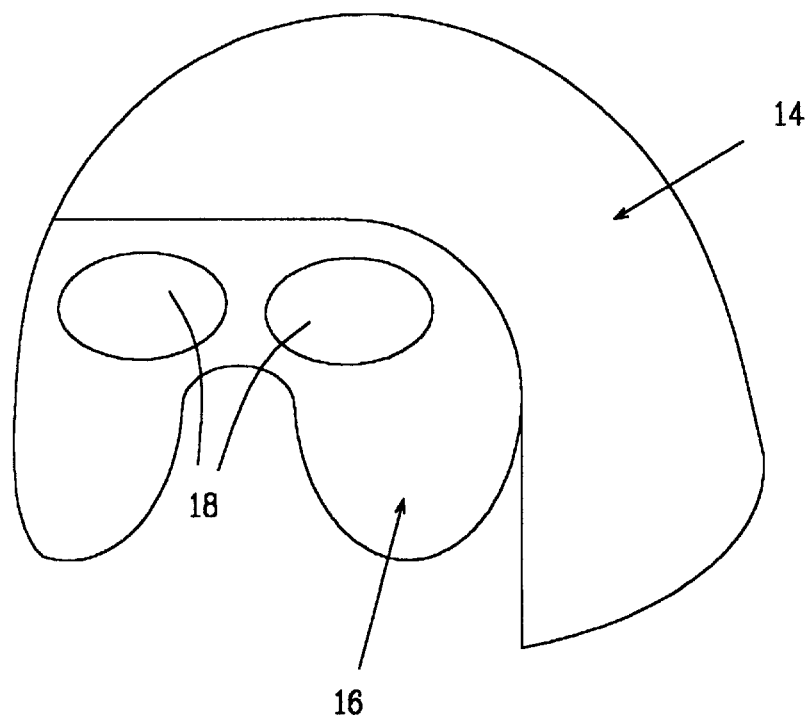
FIG. 2 is an illustration of a second embodiment of eye protection gear using the invention.

FIGS. 1 and 2 illustrate two of many forms of optical protective gear specifically and particularly available for pilots. Eyeglasses 10 have lenses 12 that may be made of the optical limiters of this invention. Lenses 12 will pass electromagnetic radiation in the visible spectrum (light) but will react to high intensity laser radiation and block the laser light. Blocking can occur as a result of numerous phenomena, two of which include: a) photo-reactive ions which undergo excited state absorption when exposed to laser radiation, and b) photo-reactive ions which photo-ionize when exposed to laser light resulting in new absorption bands which have strong absorption characteristics at the wavelength of the laser light. Similarly, the aviator helmet 14 of FIG. 2 has a visor 16, which may be fabricated of crystals 18 of this invention; or visor 16 may have crystals 18 of this invention laminated onto a visor support layer, and thus may serve as an optical limiter carrier.

Figure 3:
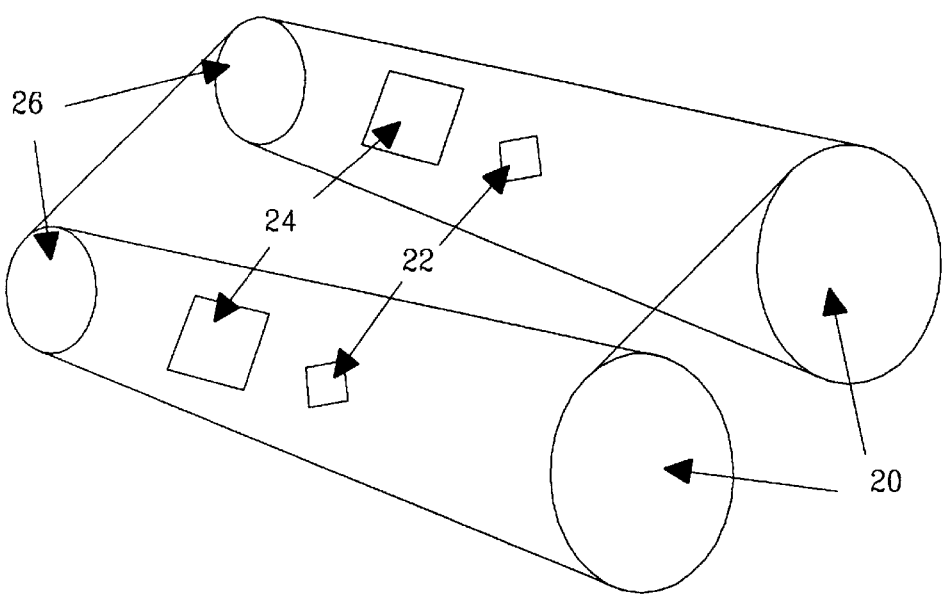
FIG. 3 is an illustration of a third embodiment of eye protection gear using the invention.

In some cases, it is possible for the laser power to be sufficient to damage optical receptors but for the intensity (power per unit area) to be insufficient to induce optical limiting in the doped inorganic materials of this invention, In such a case, it is necessary to use an optical system to increase the intensity of the laser light in the optical limiter to "turn on" the optical limiting process. FIG. 3 shows an example of goggles that incorporate such a system. The direct view goggles 20 of FIG. 3 have an objective lens 22 that focuses the laser light into the optical limiter material 24. The image inverter 26 restores the image to its original orientation and the ocular system 28 provides the desired image for viewing by the wearer of the goggles 20. This is only one of many types of optical systems that could be employed to focus the laser light into the limiter material.

It has been discovered that in some organic materials, which when doped with photo-reactive ions and upon exposure to high intensity levels of laser radiation, undergo a change such that the transmission of the laser light is substantially reduced. Such active ions include transition metal ions and, particularly, ions of Mn in the 3+, 4+ and 5+ valance states. These dopants may be incorporated into an amorphous material or the host lattice of an inorganic crystalline material. These materials may be fabricated to produce light transmissible members such as a lens 12 or crystals 18 and optical limiter material 24.

Figure 4:
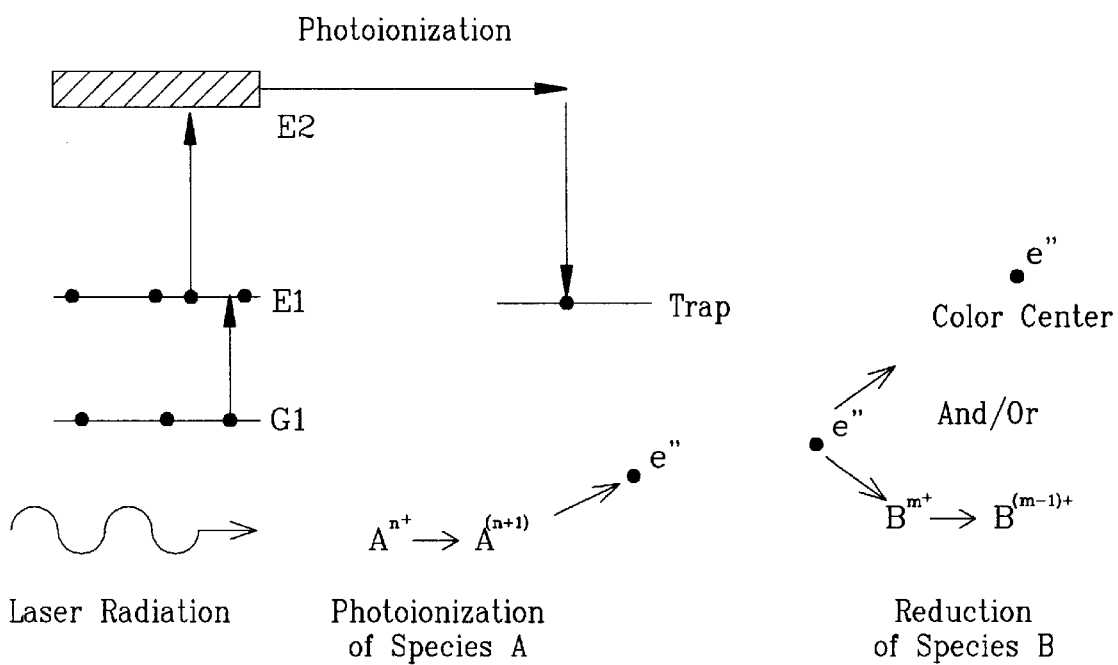
FIG. 4 is a conceptual diagram of the photo-reactive process of blocking laser radiation.

A conceptual operation of the invention is illustrated in FIG. 4 which shows a schematic diagram of the types of processes in these materials. In this case, laser radiation incident on the doped inorganic material is absorbed by the dopant ions (species A) exciting electrons in the ions from the ground state G1 to an excited state E1. Ions with electrons in the excited state E1 then absorb additional laser light exciting the electrons to a second excited state E2. This ESA process results in optical limiting of the laser light and can be very rapid, occurring on a sub-nanosecond time scale, allowing the material to block intense light pulses from Q-switched lasers. Ions in the E2 excited state are then photoionized from an initial valance state N+to an final valance state $(N+1)^+$. The free electron created during photoionization of the dopant ion is then trapped forming a color center or captured by another ion (species B) reducing it from an $M^+$ to an $(M-1)^+$ ionization state. Both the color center or reduced ionic species B and the photo-ionized dopant ion have optical properties different from that of the original substantially transparent doped host material. In some cases, these optically induced color centers and/or ion sites act as strong broadband absorbers at the laser wavelength, providing additional reduction in the transmission of laser radiation. Recovery of the doped host material to its original state is accomplished by reduction of the original photo-ionized dopant ion by freeing the electron from the trap. Upon complete reduction, the transparency of the material is restored. This reduction may occur spontaneously or may require some additional source of energy depending on the nature of the electron trap. For example, recovery may be assisted by heating of the exposed material. This characteristic of recovery permits reuse of these protection devices at a minimal cost.

Transition metal ions are good candidates for use in these processes since they exist in multiple valence states allowing for photo-ionization and have many absorption bands such that combinations of spin-forbidden/spin-allowed transitions exist which allow for strong excited state absorption in the visible and IR spectral regions. When incorporated in an appropriate host, these ions can have valence states which are transparent in a given spectral region of interest as well as valence states with broad absorption bands in the same spectral region. Inorganic crystalline materials doped with transition metal ions were used for demonstration of this invention. Mn was chosen as a preferred dopant ion because it is among the most easily photoionized of the transition metals. The crystals were grown using the Czochralski crystal growth process, which is a well known process to those skilled in the art of crystal growth.

The host crystals used in the demonstration of this invention include $YAlO_3$, $Y_3Al_5O_{12}$ (YAG), and $Gd_3Ga_5O_{12}$ (GGG). While each of these host crystals can contain and support transition metal dopant ions, the photo-response of the doped crystals are dependent upon the combination of the doping ion or ions and the host crystal lattice selected to incorporate the dopant ions.

These host materials are well developed exhibiting thermally and mechanically robust properties with high optical damage thresholds and are known to readily incorporate transition metal ions in multiple valance states. The $YAlO_3$ and GGG host materials are well known for their propensity to form color centers which can charge compensate dopant ions or provide a trap for the electron from a photoionized dopant ion. As a result, these hosts doped with transition metal ions are good candidates for optical limiting via processes involving ESA, photoionization, color center formation and combinations of these processes. The predominate mode or modes of light limiting is determined by the combination of dopant ions and host crystal matrix.

For purposes of optical limiting, it may be advantageous to incorporate either single or multiple species of dopant ions into the host material. Since recent advances in laser technology have resulted in lasers which can emit at a variety of wavelengths, it may be necessary to optically limit over the entire visible region of the spectrum in order to protect human eyes. These materials have the advantage of offering this capability. The choice of the dopant ion or ions will dictate the optical limiting properties and observed color of the material. A single dopant ion will have specific bands in the visible and IR spectrum over which optical limiting will occur. The use of multiple dopant ions, co-doping, may allow for a broader band of optical limiting. In the visible spectral region, co-doping also allows for modification of the color of the optical limiter material to provide a neutral density appearance that does not alter the colors of images viewed through the material.

A typical example of the technique employed for the fabrication of a doped crystalline optical limiter is described as follows: A quantity of yttria ($Y_2O_3$) and alumina ($Al_2O_3$) in a 1:1 ratio ($YAlO_3$) was melted along with 1.0% by weight of manganese dioxide ($MnO_2$). A crystal containing Mn as the dopant was grown from this melt using the Czochralski crystal growth process. The resulting crystal (Mn:$YAlO_3$) was substantially transparent to visible light with a pale yellow color. Test samples were cut from the crystal and polished to a smooth surface condition to render them transparent to visible light. The polishing technique is conventional and well known in the optics field for polishing lenses as for eyeglasses.

The spectroscopic and optical limiting properties of the $YAlO_3$ sample were characterized by analyzing the transmission intensity and spectrum of the sample upon exposure to white light (low level visible light), continuous wave lasers, and high-energy Q-switched pulsed lasers. Exposure of this material to light from a continuous wave argon ion laser at a wavelength of 514.5 nm resulted in the crystal very rapidly turning opaque to a substantial portion of the visible spectrum. After exposure, the crystal was a dark blue in the exposed region.

Figure 5:
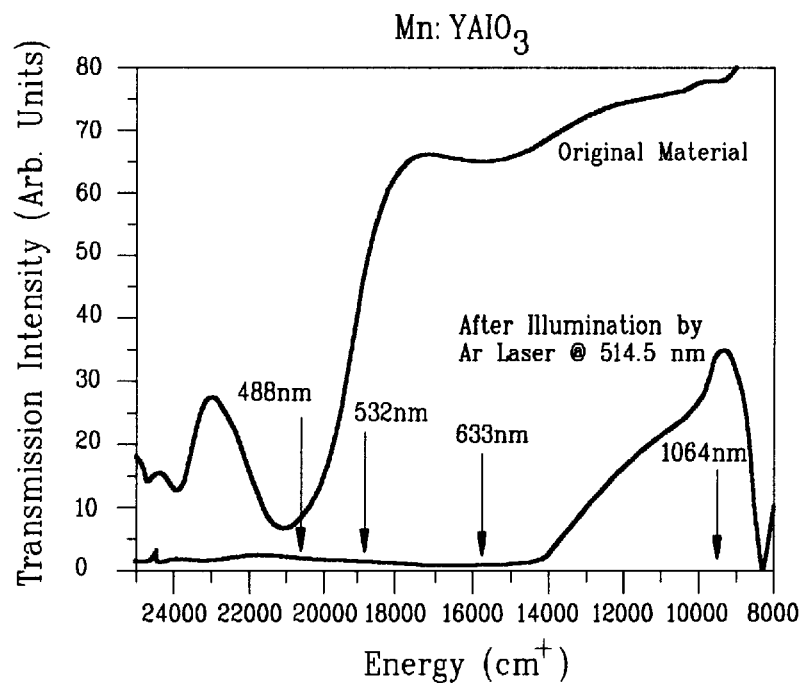
FIG. 5 is an absorption spectrum of the material Mn:$YAlO_3$ before and after exposure to an argon ion laser at 514.5 nm.

Measurements of white light transmission after this exposure showed that less than 3% of the white light was being transmitted in the visible spectral region from 400 nm to 700 nm as shown in FIG. 5. In the region from 550 nm to 600 nm, the transmission of light was reduced to less than 0.5%. The reduction in transmission occurred only in the region of the sample which was exposed to the high intensity light of the laser.

This process was shown to be reversible by heating the sample to a temperature of about 250° C. for less than three (3) minutes. After this heating cycle, the photo-transformed region was restored to its original transparency and pale yellow color. Upon re-exposure of the material to the high intensity laser light, the sample again exhibited the changes, optically limiting the transmission of the laser radiation.

Exposure of the Mn:$YAlO_3$ to the 488 mn and 457 nm emission lines of the argon ion laser resulted in a qualitatively similar optical limiting response as observed for exposure to the 514.5 nm laser light.

Characterization of the Mn:$YAlO_3$ was also performed using a Q-switched frequency-doubled Nd:YAG laser operating at 532 nm. Measurements were made to determine the transmission properties of this material as a function of incident laser energy. The energy and temporal profile of the incident and transmitted pulses were monitored to characterize the average and time resolved response of the material.

Figure 6:
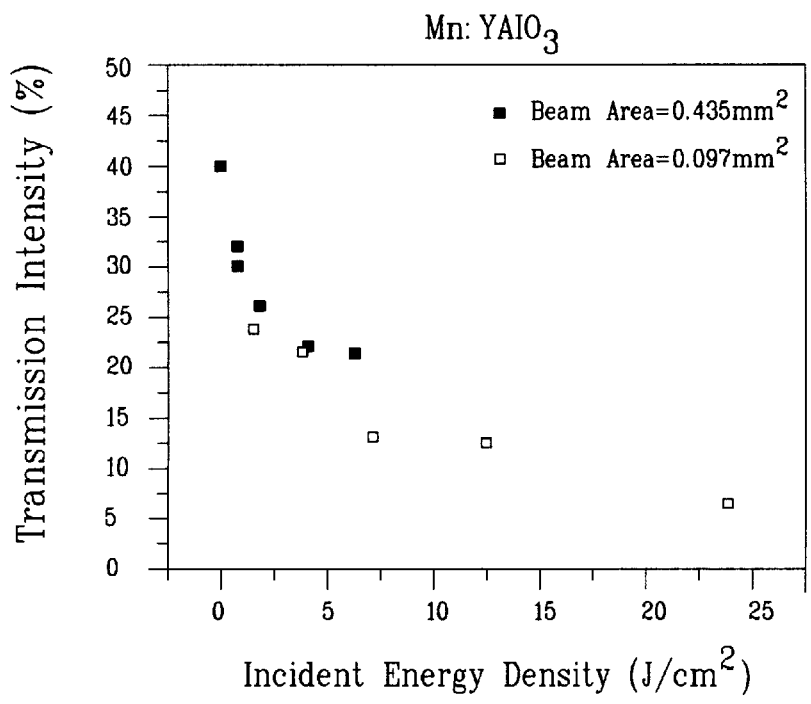
FIG. 6 shows the transmission of 10 ns long 532 nm laser pulses through Mn:$YAlO_3$ as a function of incident pulse energy density.

FIG. 6 shows a plot of the relative transmission for Mn:$YAlO_3$ as a function of incident energy density. The transmission of this material was intensity dependent and attenuated the transmission of Q-switched nanosecond pulses by more than an order of magnitude.

Figure 7:
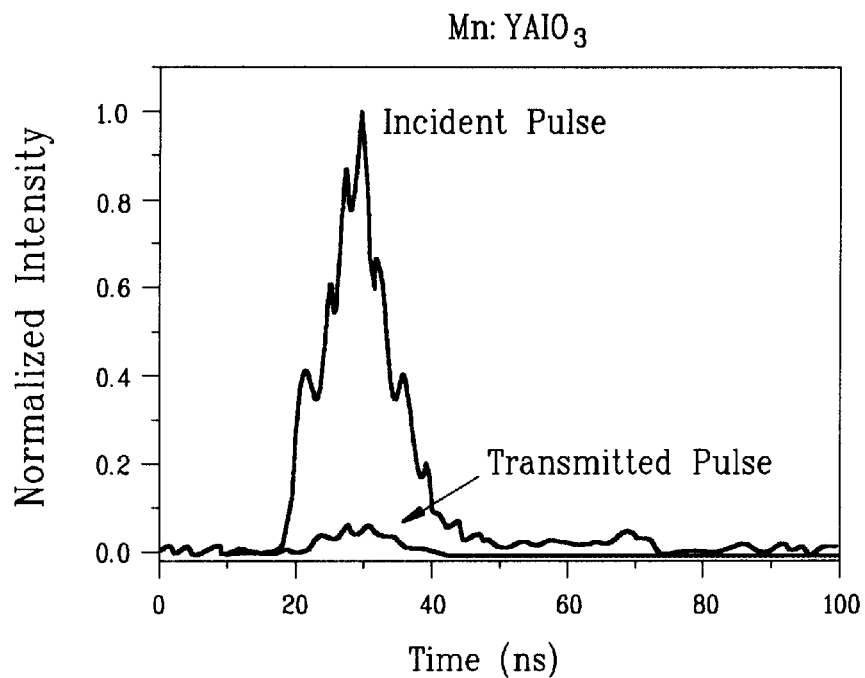
FIG. 7 shows the time resolved transmission intensity at 532 nm for Mn:$YAlO_3$ demonstrating optical limiting by more than one order of magnitude on a time scale faster that the rise time of the laser pulse.

The speed at which a doped crystal reacts to the illumination of the laser light is important in protecting eyesight and optical sensors. Damage done to the human eye or optical sensors may occur within a relatively short period of time if the intensity of the laser light is sufficiently high. FIG. 7 is a typical time resolved trace showing the normalized temporal profile of the incident laser pulse (the laser light intensity versus time at the entrance or first surface of the specimen) and the transmitted laser pulse (the laser light intensity versus time at the exit or second surface of the specimen) for the Mn:$YAlO_3$ crystal. The temporal profile of the transmitted beam matched that of the incident beam to within the detection limits of the system indicating that the optical limiting occurred on a time scale faster than the rise time of the laser pulses. This corresponds to a response time for the material that was subnanosecond and which was limited by the temporal resolution of the detector and electronics. It is also important to note that exposure of this material to single shots of Q-switched laser output did not result in significant transformation of the material to the dark blue observed after exposure to the argon laser beam; however, the doped crystal optically limited the pulsed laser radiation, thereby preventing transmission of significant amounts of the radiation with an attenuation of at least 15:1. Low intensity transmission experiments conducted after exposure to single Q-switched shots showed only a few percent decrease in the transmitted intensity.

Figure 8:
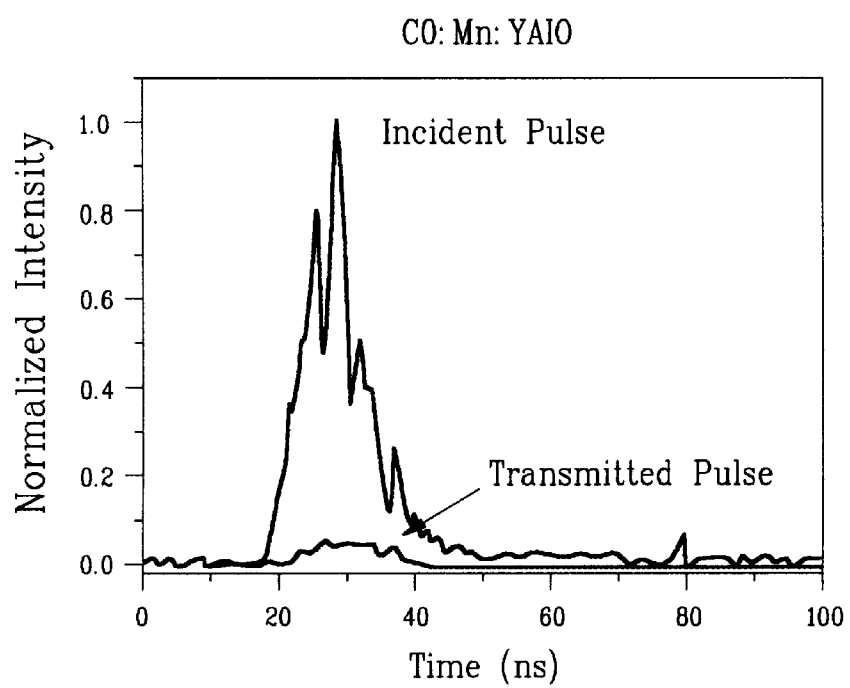
FIG. 8 shows the time resolved transmission intensity at 532 nm for the codoped material Co:Mn:$YAlO_3$ demonstrating optical limiting by more than one order of magnitude on a time scale faster hat the rise time of the laser pulse.

A crystal of $YAlO_3$ co-doped with 0.5% by weight Co and 1.0% by weight Mn was also grown as described previously to demonstrate the ability to use multiple dopant ions to manipulate the color of the optical limiter materials. The 0.5%Co:1%Mn:$YAlO_3$ crystal is substantially transparent with a neutral brown color. Samples of this crystal were prepared and the performance characteristics were determined in the same manner as described above for the Mn:$YAlO_3$ doped material. The results of the testing of the Co:Mn:$YAlO_3$ codoped crystal showed optical limiting qualitatively similar to if not better than the limiting found in the Mn:$YAlO_3$. FIG. 8 shows a typical time resolved trace comparing the incident and transmitted laser pulse temporal profiles for a codoped Co:Mn:$YAlO_3$ specimen. Similarly, Mn and Co ion co-doping in similar quantities yields a laser light limiting effect in a GGG crystal.

The optical limiting behavior observed in the Mn:$YAlO_3$ and Co:Mn:$YAlO_3$ materials was due to multiple mechanisms. In particular, ESA, photoionization of the Mn ions and trapping of the electrons by other Mn ions resulted in the observed intensity dependent attenuation of the laser beam. The formation of color centers by trapping of the electron in the lattice may also have contributed.

The first step in the limiting process was due to the presence of strong excited state absorption which is an intermediate step in the photo-ionization process. As noted previously, this mechanism itself may be exploited for optical limiting in inorganic crystals doped with transition metal ions. The Mn ions substituted for the Al ions of the $YAlO_3$ lattice and were incorporated in the 4+ valance state. The $Mn^{4+}$ dopant ions are initially in the $^4A_2$ ground state (lowest energy state). When exposed to laser radiation at 532 nm the $Mn^{4+}$ ions absorb light, exciting them to the higher energy $^4T_2$ state. This $^4A_2 \rightarrow {}^4T_2$ transition results in the absorption peak at ~480 mn in Mn:$YAlO_3$ giving the material its initial pale yellow color. The absorption characteristics of the $Mn^{4+}$ ions in this higher energy intermediate level are different than absorption characteristics for the ions in the ground state. In particular, whenever a sufficient number of ions are in the intermediate energy state, the transmission of high intensity laser radiation is limited by the onset of strong excited state absorption. This occurs because the absorption bands corresponding to transitions from the $^4T_2$ excited state to even higher energy excited states overlap the wavelength region of the ground state absorption band.

A second step in the limiting process involves photoionization of the $Mn^{4+}$ ions and charge transfer of the electron to other $Mn^{4+}$ ions or to traps in the lattice. The color change of the Mn:YAlO$_3$ from yellow to blue-gray upon exposure to laser radiation in the absorption band peaked at 480 nm is due to photoionization of the Mn$^{4+}$. Following ESA, the Mn$^{4+}$ ions in the second excited state are photoionized creating an Mn$^{5+}$ ion (Mn$^{4+}$→Mn$^{5+}$+e$^-$). The free electron is then trapped on another Mn$^{4+}$ ion creating an Mn$^{3+}$ ion. It is also possible that the free electron is trapped in the lattice forming color centers. The absorption spectra in FIG. 4 for the photo-transformed Mn:YAlO$_3$ results from a combination of the spectra for Mn$^{3+}$, Mn$^{4+}$, Mn$^{5+}$ and any color centers that have formed. The Mn$^{5+}$ has a very broad absorption band peaked at 630 nm; the Mn$^{3+}$ absorption maximum is at ~530 nm; and the Mn$^{4+}$ absorption maximum is at ~480 nm. This combination results in the grayish blue color of the photo-transformed Mn:YAlO$_3$. The formation of the Mn$^{3+}$, Mn$^{5+}$, and color centers act to further limit the transmission of the incident laser light.

While some low level of excited state absorption or photo-ionization may occur at low illumination levels, the material remains substantially transparent with the transmitted light attenuated only by the ground state absorption spectrum that is responsible for the observed color of the material. With illumination by high intensity laser light, the population of the ions in the intermediate level increases and strong attenuation of the laser light occurs. These spectral characteristics are typical of crystals doped with transition metal ions.

Figure 9:
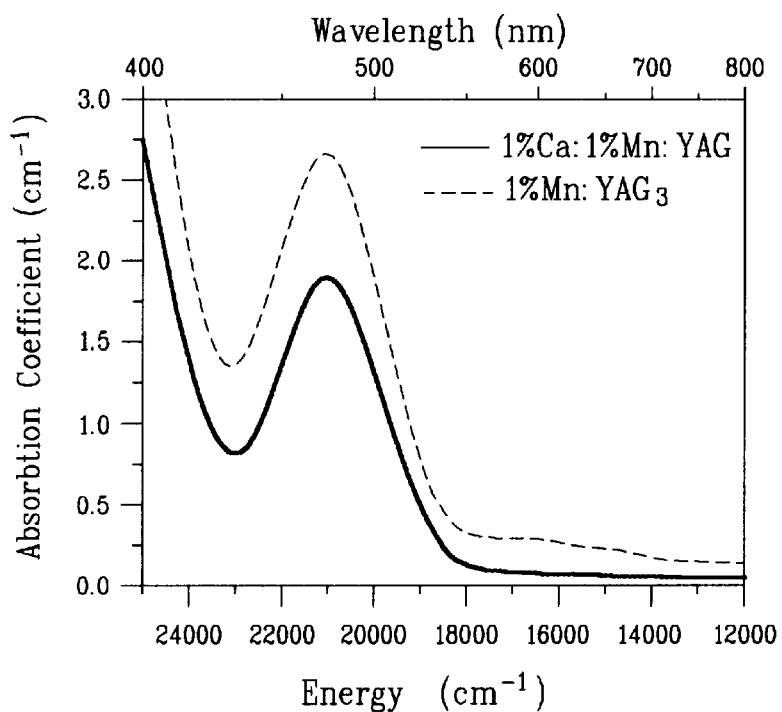
FIG. 9 shows an absorption spectra for 1%Ca:1%Mn:YAG compared with a spectrum from the Mn:$YAlO_3$ crystal.

Optical limiting was also demonstrated for crystals of YAG co-doped with Mn and Ca and for crystals of GG0 doped only with Mn and co-doped with Mn and Ca. A crystal of YAG was grown using conventional Czochialski crystal growth techniques from a melt that contained quantities of yttria (Y$_2$O$_3$) and alumina (Al$_2$O$_3$) in a 3:5 ratio (YAG) that was co-doped with 1.0 atomic % Ca and 1.0 atomic % Mn. The YAG lattice has three types of cation sites; dodecahedral sites occupied by Y$^{3+}$ ions, octahedral sites occupied by Al$^{3+}$ ions and tetrahedral sites also occupied by Al$^{3+}$ ions. The Ca is a 2+ ion that substitutes for the Y$^{3+}$ on the dodecahedral sites. The Ca$^{2+}$ charge compensates the Mn ions allowing it to substitute for the aluminum as a 4+ ion. This has also been accomplished by using Mg$^{2+}$ to charge compensate the Mn$^{4+}$. The Mn, Ca co-doped YAG crystal was yellow in color, very similar to the color of the Mn:YAlO$_3$. FIG. 9 shows absorption spectra for the 1%Ca:1%Mn:YAG compared with a spectrum from the 1% Mn:YAlO$_3$. The absorption spectra from the YAG sample was almost identical to that of the YAlO$_3$. These spectra confirm that the Mn was incorporated as a 4+ ion since the peak is shifted to the blue compared to the absorption of Mn$^{3+}$ in YAG. Exposure of the 1%Ca:1%Mn:YAG crystal to laser radiation in the green and blue (using an argon laser at 514 nm and 488 nm) did not result in any darkening of the material as occurs in the Mn:YAlO$_3$.

Figure 10:
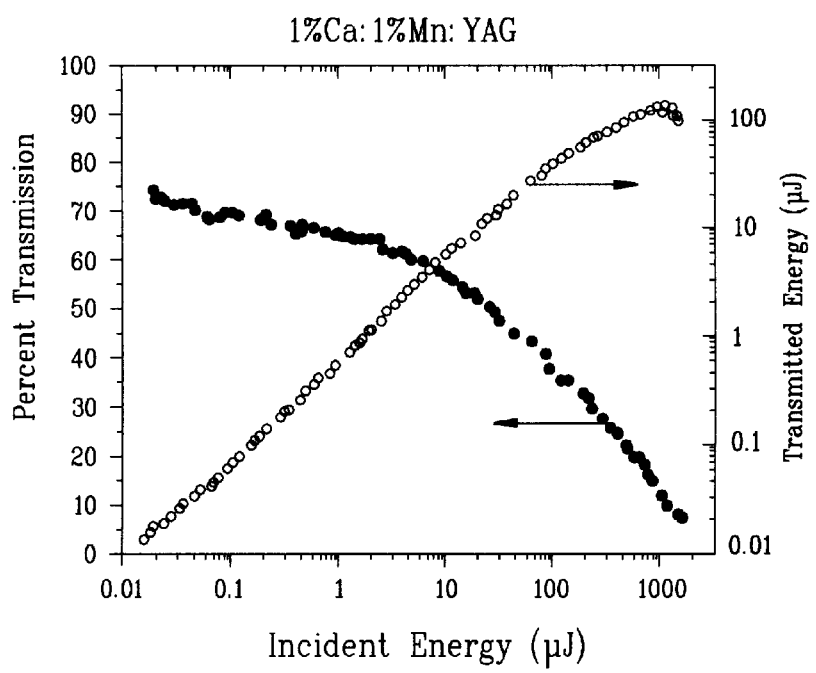
FIG. 10 shows the percent transmission and transmitted energy versus incident energy for a 1%Ca:1%Mn:YAG crystal.

Optical limiting performance of the 1%Ca:1%Mn:YAG was characterized using measurement protocols that were implemented according to the NATO Research Study Group 19 (RSG-19) specifications. This protocol uses an f/5 optical system to focus the laser light into the test sample. Incident and transmitted laser pulse energies were measured using a Laser Probe model Rm-6600 energy meter equipped with rjp-465 or rjp-435 detectors. Testing was performed at 532 nm using a Q-switched frequency doubled Nd:YAG laser that emitted pulses with a duration of approximately 15 ns. FIG. 10 shows percent transmission and transmitted energy versus incident energy for 1%Ca:1%Mn:YAG. Although the initial transmission was higher in the YAG material compared to YAlO$_3$ (most likely because of lower Mn$^{4+}$ concentration), the decrease in transmission with increased laser energy appears to be even more rapid in the YAG indicating that it may perform better as an optical limiter material.

The optical limiting observed in the 1%Ca:1%Mn:YAG for the Q-switched Nd:YAG laser pulses at 532 nm was primarily due to ESA as described previously for the Mn:YAlO$_3$. This was verified by obtaining a transient absorption spectra on time scales ranging from several nanoseconds to hundreds of seconds following exposure to laser radiation. White light absorption spectra were obtained both during and following exposure of the 1%Ca:1%Mn:YAG to a 3 ns Q-switched laser pulse at 532 nm from a frequency doubled Nd:YAG laser. Spectra were also obtained during and following exposure of this material to a continuous wave argon ion laser at 514.5 mn.

These spectra showed that ESA bands formed during and immediately following exposure to the Q-switched laser pulses and a few seconds of exposure to the argon laser. Longer exposure (10's to 100's of seconds) by the argon laser resulted in decreased ESA and the formation of other ionic species. Thus on a short time scale the observed optical limiting is dominated by ESA processes and charge transfer processes are the predominate limiting mechanism, on a long time scale.

Figure 11:
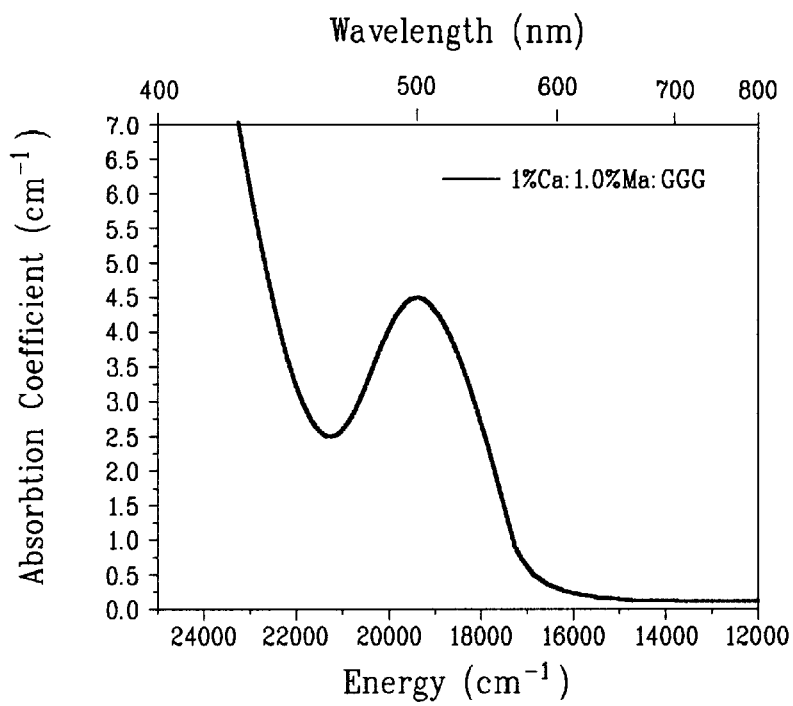
FIG. 11 shows an absorption spectra for a 1%Ca:1%Mn:GGG crystal.

A crystal of GGG was grown using conventional Czochlalski crystal growth techniques from a melt that contained quantities gadoliniuin oxide (Gd$_2$O$_3$) and gallium oxide (Ga$_2$O$_3$) in a 3:5 ratio (GGG) doped with 1 atomic % Ca and 1 atomic % Mn in the melt. Spectroscopic and optical limiter test samples were fabricated and characterized. FIG. 11 shows a white light absorption spectra for the 1%Ca:1%Mn:GGG crystal. This host was anticipated to have a weaker crystal field at the dopant ion site. This was confirmed by the fact that the absorption band peaked at 480 nm in YAG shifted to lower energy at 510 nm in GGG which is consistent with the predicted behavior from the Tanabe-Sugano diagram for a d$^3$-electron configuration. Because of the shift in the ground state absorption band to lower energy, the 1%Ca:1%Mn:GGG crystal was slightly more orange in color compared to the same doping in YAG.

Figure 12:
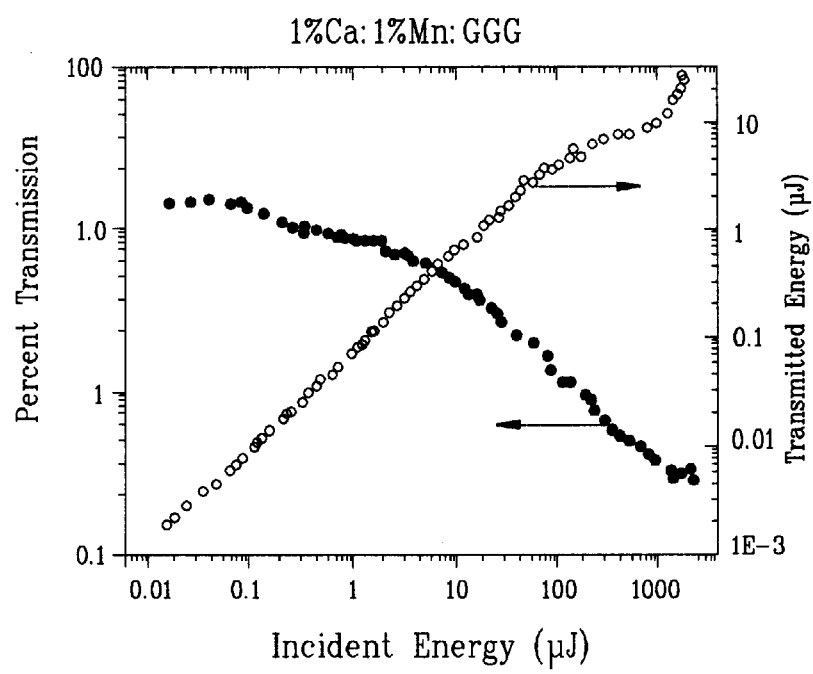
FIG. 12 shows the percent transmission and transmitted energy versus incident energy for a 1%Ca:1%Mn:GGG crystal.

Optical limiting performance of the 1%Ca:1%Mn:GGG was characterized using measurement protocols that were implemented according to the NATO Research Study Group 19 (RSG 19) specifications as described above. Fig. 12 shows the percent transmission and transmitted energy versus incident energy for the 1Ca:1%Mn:GGG crystal. This material transmitted less than 7$\mu$J for all input energies up to the damage threshold of the material. It is important to note that this result was obtained for a material that has not been optimized. It is projected that an order of magnitude improvement in performance can be obtained through a combination of material optimization and optical design. This crystal had good transparency in the visible spectrum, transmitting approximately 50% of the visible light in the wavelength range from 400 nm to 700 nm for a 3 mm thick sample. Visually/qualitatively, the material preserved color information and images were bright and clear when observed through a window of the material. This dopant host combination 16 appears to have great potential for real device applications.

Optical limiting in the 1%Ca:1%Mn:GGG crystal was due to similar processes as observed in the Mn:YAlO$_3$. In particular, ESA and subsequent photoionization of the Mn$^{4+}$ ions contributed to the observed intensity dependent reduction in laser transmission. Charge transfer of the electron released by photoionization of the $Mn^{4+}$ ions to other $Mn^{4+}$ ions and to traps in the lattice resulted in photo-induced absorption bands that further limited the transmission of the incident laser radiation. Mn:Mg:Ca co-pending of $YAlO_3$, $Y_3Al_5O_{12}$, or $Gd_3Ga_5O_{12}$, when resident in quantitites of about 1% Mn ions and sufficient charge compensations quantities of the Mg and Ca ions to maintain the Mn ions in a 4+state also produces laser light limiting in the range of 400–550 nm due to the presence of the $Mnn^{4+}$ ions present in the selected host material by the charge compensation effects of the Mg and Ca ions.

Mn and Mg ions, when resident in similar quantities and hosted by a $YAlO_3$ crystalline host also has the properties of overlapping ground state absorption and excited state absorption bands and functions as a light limiter, limiting laser light in the overlapping regions.

Characterizations of the spectroscopic and optical limiting performance in the materials used to demonstrate this invention were performed for a single concentration of the active dopant ions. The quantity of dopant ions incorporated into the host matrix can vary over a wide range. This concentration of dopant ions will determine the ground state or conventional absorption characteristics and thus affects the intensity and color of the low levels of light which pass through the crystal. The concentration will also effect the optical light limiting properties. Moreover, it is possible to determine the optimal amount of the dopant ions incorporated to optimize the optical light limiting properties of the material. The further addition of dopant ions to increase the concentration will also limit the transmission of lower levels of light as a neutral density filter.

Optimization of the dopant ion concentration will allow for the thickness of an optical limiter to be reduced. This permits the optical limiter crystals to be fabricated into relatively lightweight lenses or pieces for positioning on the head of the wearer such that the weight of the optical limiting device does not become excessive, thus allowing for wearer comfort.

We claim:

1. A method of limiting the passage of laser light through a solid substantially transparent medium in response to said laser light having a selected wavelength impinging on said medium comprising the steps of:

inserting into a path of a laser light beam said substantially transparent medium, said substantially transparent medium having incorporated therein a dopant of ions at least one transition metal, said medium being an inorganic crystal; said ions exhibiting ground state absorption over a first band of light wavelengths; said ions further exhibiting excited state absorption over a second band of light wavelengths, said first band of light wavelengths and second band of light wavelengths overlapping; said overlapping bands of said ground state absorption and said excited state absorption both including the wavelength of said laser light to be limited;

said transparent material selected from a group consisting of $YAlO_3$, $Y_3Al_5O_{12}$ and $Gd_3Ga_5O_{12}$, and said dopant comprises ions selected from the group consisting of $Mn^{4+}$; Mn and Ca; Mn and Mg; Mn and Ca and Mg; and $Mn^{4+}$ and Co;

receiving sufficient intensity of said laser light beam onto said medium to cause excited state absorption of said laser light beam by exciting said ions from a ground state to an excited state and absorbing a portion of said laser light beam, and absorbing a further portion of said light of said laser beam by said ions in said excited state to non-linearly absorb said laser light, thereby limiting the transmission of said laser light through said medium.

2. The method of claim 1 wherein said substantially transparent material is $YAlO_3$.

3. The method of claim 1 wherein said substantially transparent material is $Y_3Al_5O_{12}$.

4. The method of claim 1 wherein said substantially transparent material is $Gd_3Ga_5O_{12}$.

5. The method of claim 2 wherein said dopant ions are ions of Mn.

6. The method of claim 2 wherein said dopant ions are comprised of ions of Mn and Ca.

7. The method of claim 2 wherein said dopant ions are comprised of ions of Mn and Mg.

8. The method of claim 2 wherein said dopant ions are comprised of ions of Mn, Ca, and Mg.

9. The method of claim 2 wherein said dopant ions are comprised of ions of Mn and Co.

10. The method of claim 3 wherein said dopant ions are ions of Mn.

11. The method of claim 3 wherein said dopant ions are comprised of ions of Mn and Ca.

12. The method of claim 3 wherein said dopant ions are comprised of ions of Mn and Mg.

13. The method of claim 3 wherein said dopant ions are comprised of ions of Mn, Ca and Mg.

14. The method of claim 3 wherein said dopant ions are comprised of ions of Mn and Co.

15. The method of claim 4 wherein said dopant ions are comprised of ions of $Mn^{4+}$.

16. The method of claim 4 wherein said dopant ions are comprised of ions of $Mn^{4+}$ and Ca.

17. The method of claim 4 wherein said dopant ions are comprised of ions of $Mn^{4+}$ and Mg.

18. The method of claim 4 wherein said dopant ions are comprised of ions of $Mn^{4+}$, Ca and Mg.

19. The method of claim 4 wherein said dopant ions are comprised of ions of $Mn^{4+}$ and Co.

* * * * *